United States Patent [19]

Suzuki et al.

[11] 4,347,259

[45] Aug. 31, 1982

[54] METHOD FOR REDUCING THE BACTERIAL POPULATION OF BLOOD POWDER

[75] Inventors: Yoshio Suzuki, Kamakura; Masao Shimizu, Yokohama, both of Japan

[73] Assignee: Niigata Engineering Co., Ltd., Tokyo, Japan

[21] Appl. No.: 112,254

[22] Filed: Jan. 15, 1980

Related U.S. Application Data

[63] Continuation-in-part of Ser. No. 77,809, Sep. 21, 1979, abandoned, which is a continuation of Ser. No. 925,338, Jul. 17, 1978, abandoned.

[30] Foreign Application Priority Data

Jul. 16, 1977 [JP] Japan .................................. 52/85388

[51] Int. Cl.³ .............................................. A23B 4/00
[52] U.S. Cl. .................................... 426/465; 426/521; 426/647; 260/112 B
[58] Field of Search ............... 426/465, 471, 472, 473, 426/647, 521, 32; 260/112B

[56] References Cited

U.S. PATENT DOCUMENTS 1,632,321 6/1927 Sternberg ............................ 426/473
3,950,555 4/1976 Stromberg ........................... 426/647

OTHER PUBLICATIONS

Von Loesecke, *Drying and Dehydration of Foods*, "Bacteria in Dried Blood", pp. 200 and 201, 1943.
Braverman, *Introduction to the Biochemistry of Foods*, "Inactivation of Enzymes by Heat", pp. 169 and 170, 1963.

*Primary Examiner*—Raymond N. Jones
*Assistant Examiner*—George C. Yeung
*Attorney, Agent, or Firm*—Sughrue, Mion, Zinn, Macpeak and Seas

[57] ABSTRACT

A method for reducing the bacterial population of a blood powder having a moisture content of about 30% by weight or less, comprising heating the powder at a heating temperature of about 80 to about 160° C. for a period of time to reduce the bacterial population of the blood powder so as to obtain blood products having a solubility of at least 50% without denaturing the blood protein. The blood product is useful for a foodstuff material and a rheological binding agent suitable for the improvement of the quality of a processed foodstuff.

16 Claims, 6 Drawing Figures

METHOD FOR REDUCING THE BACTERIAL POPULATION OF BLOOD POWDER

CROSS-REFERENCE TO RELATED APPLICATIONS

This application is a continuation in part of U.S. application Ser. No. 77,809, filed on Sept. 21, 1979 now abandoned, which is a continuation of U.S. application Ser. No. 925,338, filed on July 17, 1978, now abandoned.

BACKGROUND OF THE INVENTION

1. Field of the Invention

This invention relates to a method for heat-sterilizing a blood powder (e.g., plasma powder, serum powder, corpuscle powder, whole blood powder) obtained from the blood of livestock, for example, killed in slaughter-houses, in order to obtain a rheological binding agent suitable for an increase of the quality of the processed foodstuff using the blood powder.

2. Description of the Prior Art

Attempts have been made heretofore in various countries to produce blood powders from the blood of slaughtered animals and to use the powders as foodstuffs or feeds, for example. Blood powders for feeds are being produced also in some slaughter-houses in Japan. Blood powders have also been suggested for foodstuff. In recent years, there has been a worldwide need for securing sources of animal proteins. Since blood proteins are nutritionally complete proteins and have superior properties such as water solubility and heat coagulability, there has been an increasing demand for the utilization of blood powders for foodstuff. Sterilizing techniques, however, have posed a problem in utilizing blood powders in foodstuffs.

The conventional sterilizing method comprises feeding steam directly into the collected blood. However, this method causes a denaturation of the proteins, a loss of the water solubility and a loss of the heat coagulability of the blood powder which are required as foodstuffs. Hence, the usefulness of the blood powder in foodstuffs is very much reduced. Methods which have been suggested or are being performed for production of edible blood powders involve whole blood or separating the collected blood into plasma or serum and corpuscles, and drying the fractions, e.g., by spray-drying, lyophilizing or vacuum drying, separately to produce blood powders without denaturing the proteins. However, since the temperature used for concentration and drying is low, the blood powders cannot be sterilized at the temperature used. No effective technique for sterilizing such blood powders has been developed.

For example, in the case of drying foodstuffs by a spray-drying, generally, the drying is carried out using an air flow of about 150° to 180° C. but the moisture is momentarily evaporated, and as a result, the temperature of the dried product is maintained at a low temperature of about 50° to 60° C. or less by the latent heat of evaporation and never increases, and in the case of drying foodstuffs by a vacuum drying, since the boiling point is determined depending upon the vacuum degree, it is possible to limit the heating temperature of the dried product to 60° C. or less in accordance with the vacuum degree. Thus, in the above drying processes, the blood powder can be dried at 60° C. or less. However, since the temperature of the substance heated is low, a sterilizing effect cannot be obtained at all.

Water solubility and heat coagulability are among the properties of blood powder which are required for use in foods. In general proteins, these properties are easily lost by heating. Alternatively, sterilizing methods using chemicals or by filtration are conceivable. However, these alternative methods are difficult to put into practice because of the adverse effects on the human body or because of the high production cost. No effective method for sterilizing blood powders without denaturing the proteins has been developed heretofore.

SUMMARY OF THE INVENTION

It has now been found that when a blood powder having a moisture content of about 30% by weight or less is heated at a heating temperature of about 80° to about 160° C., the blood powder can be sterilized without any appreciable effect on the properties of the proteins therein such as water solubility and heat coagulability.

An object of this invention, therefore, is to provide a method for heat sterilizing a blood powder, which can surely and efficiently kill bacteria and other microorganisms including viable bacteria and Coliform bacteria without appreciably denaturing the proteins and causing a degradation of the properties, such as water solubility and heat coagulability, of the blood which are required for use in foodstuffs, and which method can lead to the ability to effectively utilize the blood powder for foodstuff.

According to this invention, there is provided a method for sterilizing a blood powder, which comprises heating a blood powder having a moisture content of about 30% by weight or less at a heating temperature of about 80° to about 160° C.

DETAILED DESCRIPTION OF THE INVENTION

Figure 1:
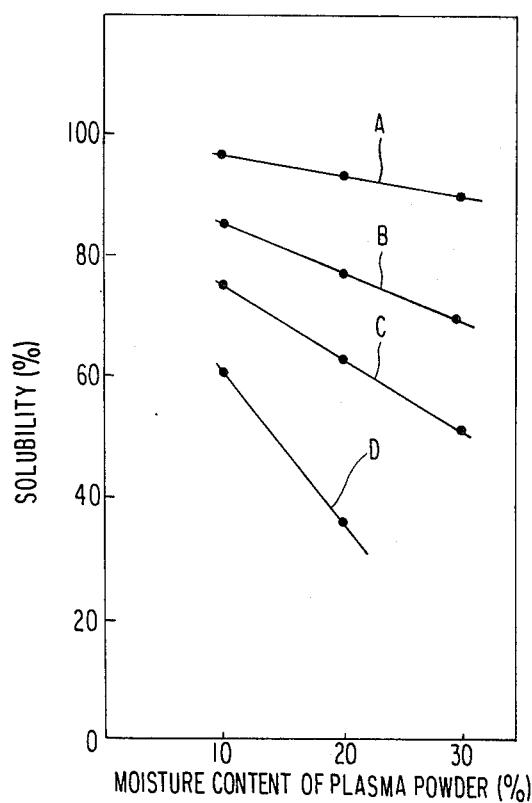
FIG. 1 is a graphical presentation showing the relationship, at different heating temperatures, between the moisture content of a plasma powder and the solubility of the plasma powder in water.

The method of this invention is applicable to plasma, serum, corpuscle and whole blood powders prepared from the blood of slaughtered livestock (herein collectively referred to as "blood powder"). The term "powder" as used in this application in the term "blood powder" refers to not only powders but also agglomerates and masses produced under the conditions disclosed herein. The definition of the "blood powder" is presented in *Chikusan Dai-Jiten* (Livestock Dictionary) published by Yokendo under the supervision of Kiyotsuna Sasaki, 1975, page 639, left column, lines 10 to 20 and Koujien (Encyclopedia), 1969, page 695, third column. In *Chikusan Dai-Jiten*, 1975, page 639, left column, lines 10 to 20, the blood powder is defined as a blood meal prepared by heating the livestock blood obtained at a slaughter-house to coagulate the blood and remove a large portion of the moisture contained in blood, and then drying the resulting blood product. In Koujien, 1969, page 695, third column, the blood powder is defined as a nitrogenous fertilizer (agglomerate and mass) in which the animal blood is evaporated to dryness.

Any of these blood powders can be well sterilized by the procedures described hereinbelow. The blood used to produce the blood powder employed in this invention can be that of basically any animal, with specific examples being that of cows, horses, pigs, sheeps, rabbits and chickens. Powders of body fluids can also be subjected to the method of the present invention, if desired.

These blood powders can be produced by the following methods. Firstly, the collected blood is subjected to a treatment to prevent coagulation.

Such a treatment can be conducted by adding an anti-coagulant to the blood (for example, an aqueous solution of sodium citrate of a concentration of about 10% by weight can be added to the blood in amount of about 10% by weight based on the blood) or the fibrins can be removed from the blood by slowly stirring the blood. The resulting blood is separated into the plasma or serum and corpuscles centrifugally, then the fractions are dried. The drying must be conducted under a low temperature of, e.g., about 60° C. or less to prevent a denaturation of the proteins. Various methods of the drying at low temperature can be used, for example, spray-drying, lyophilizing, vacuum-drying and the like. Whole blood powders can be produced by drying at a low temperature without a centrifugal separation after conducting the treatment for preventing coagulation.

Thus obtained blood powder can be formed in the various forms. However, the diameter of the blood powder obtained prior to sterilization in accordance with the present invention is not limited specifically. The diameter of the blood powder varies according to the various heating conditions, e.g., heating temperature, moisture content, a form of the powder, heating apparatus, etc.

Those blood powders having a moisture content of about 30% by weight or less, preferably 20% by weight or less, can be suitably used in this invention. If the moisture content of the blood powder is more than 30% by weight, denaturation of the proteins occurs during heat sterilization and, as a result, the water solubility is reduced. In contrast, blood powders with a moisture content of about 30% by weight or less, especially 20% by weight or less, can be sterilized under the sterilizing conditions described below without denaturing the proteins present in the blood powders.

The heat sterilization of the blood powder is performed at a heating temperature of about 80° to about 160° C., more preferably about 90° to about 145° C., most preferably about 100° to 130° C., for a period of about 10 minutes or less. When the heating temperature exceeds about 160° C., the proteins in the blood powder tend to be denatured, and the water solubility and heat coagulability of the blood powder are reduced; hence, the object of the invention cannot be achieved. The term "heating temperature" as used herein and in the examples and the claims is the temperature of the blood itself and is not ambient temperature (the term "ambient temperature" is used herein to refer to, e.g., the temperature of water bath, etc.). Longer heating periods are not advantageous because the treating time is prolonged and a large scale treating apparatus is required in commercial operations. Preferably, therefore, the heating period is about 10 minutes or less.

Sterilization of the blood powder can be performed with especially good results by heating the blood powder at a heating temperature of 100° to 130° C. The heating time which can be used within this temperature range can be varied and is not particularly limiting. More specifically, as will be apparent from the results given hereinafter in Example 1, when a blood powder is heated for 2 hours, the blood powder can be sterilized without any appreciable effect on the properties of the proteins therein such as water solubility and heat coagulability. As a result using this invention a long heating time, which might be considered to deleteriously affect the properties of the blood powder obtained, does not deleteriously affect the properties of the blood powder obtained. Accordingly, the maximum heating time is not particularly limited.

On the other hand, as shown by the results given hereinafter in Examples 2 to 5, simultaneously with reaching the specified temperature (i.e., where the heating time at the specified temperature is 0 minute), the number of bacteria present is decreased showing sterilization of the blood powder is achieved. As a result, an extremely short heating time can be effectively used in this invention. Accordingly, the heating period of time is not particularly limiting in this invention and in general a suitable heating period of time for sterilization can range up to about 4 hours and for commercial operation is about 10 minutes or less, preferably 5 to 10 minutes. Under these conditions, Coliform bacteria can be completely killed, and the blood powder can be sterilized well without any appreciable denaturation of the proteins and without any appreciable reduction in or loss of solubility in water and heat coagulability. Hence, this is an especially preferred embodiment of the method of this invention.

When the product of the present invention is mixed with the foodstuff, a simple mixture is not produced because the product has a water solubility without causing the heat denaturation. Therefore, the product of the present invention improves the rheological properties of the foodstuff as well as the above properties. That is, the product of the present invention is very useful for improving the quality of the foodstuff in food processing and can be used as a binder of various foodstuffs (for example, as a binder for sausage).

In accordance with the present invention using a blood powder having a moisture content of 30% or less, it is possible to heat the blood powder to heating temperatures greater than 80° C. and thereby sterilize the blood powder without heat-denaturation and, thus, a blood powder having a high water-soluble content suitable for use as a foodstuff is obtained.

The following Examples are given to more specifically illustrate the present invention. In the following Examples, a Batch-type stirred heating device was used in Examples 1 to 6 and Comparative Example 1, and a Continuous-type stirred heating device was used in Example 7.

(I) Batch-type stirred heating device

Figure 5:
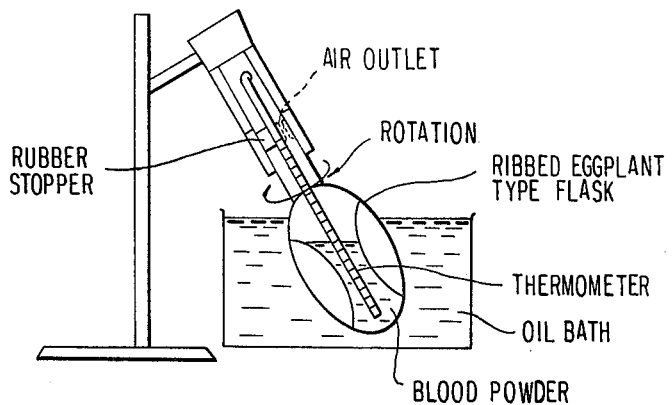
FIG. 5 is a batch-type stirred heating device.

The flask used in this comparative experiment is an eggplant type flask equipped with an inside pleat to stir the samples sufficiently. This ribbed eggplant type flask is equipped with a rotary machine to rotate it slowly. A large portion of the ribbed eggplant type flask equipped with a rotary machine is immersed into an oil bath as described below. The heating of the blood powder is carried out through the wall of the flask by increasing the temperature of the oil bath with heater. In this case, since a pleat is attached to inner wall, the blood powder is sufficiently stirred and the heating is sufficiently and uniformly carried out. The temperature of the blood powder was measured by inserting the thermometer into the blood powder as illustrated in FIG. 5.

(II) Continuous-type stirred heating device

Figure 6:
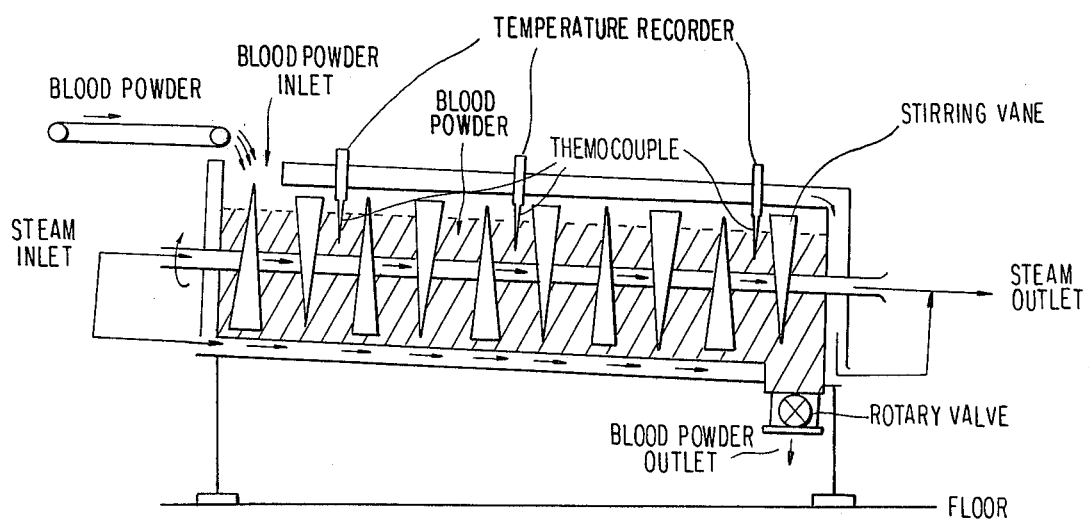
FIG. 6 is a continuous-type stirred heating device.

This heating apparatus is an apparatus capable of stirring a blood powder by rotating the shaft equipped with paddles. These paddles are not augers, but are vanes used merely to stir a blood powder. Therefore, it is carried out by inclining the heating apparatus to transfer the stirred blood powder to the outlet of the apparatus. Steam or another heated media is passed through the shaft, paddles and jacket making up the apparatus as illustrated in FIG. 6. Accordingly, the blood powder is heated uniformly by stirring with paddles and, as a result, since the stirring function of the paddles is strong, the heating of a blood powder is very quickly carried out. This heating apparatus can sterilize the agglomerates and mass of the blood as well as the powder of the blood.

The temperature of the blood powder is measured directly by providing an opening for introducing thermocouple on the upper portion of the heating apparatus, attaching the thermocouple to the apparatus, and setting it so as to insert the head of the thermocouple completely into the blood powder.

Unless otherwise indicated herein, all parts, percents, ratios and the like are by weight, and the temperature is a heating temperature of blood powder itself.

EXAMPLE 1

Plasma powders, corpuscle powders and whole blood powders were prepared from the blood of a cow with vacuum drying. In this case, a non-heated plasma powder having a moisture content of 9.7% has a solubility of 98%, a non-heated plasma powder having a moisture content of 5.7% has a solubility of 98% and a non-heated whole blood powder having a moisture content of 6.6% has a solubility of 98%. These powders were adjusted to powders having various moisture contents. The prepared blood corpuscle powder having a moisture content of 10 to 30% forms small granules, the prepared blood plasma having a moisture content of 10% is a powder, the prepared blood plasma having a moisture content of 20% to 30% is a powder containing a granular material and the amount of the granules increases according to the increase in moisture content of the prepared blood powder. The diameter of the granules prepared having a moisture content of 30% is 5.5 mm or less. The plasma, corpuscle and whole blood powders having various moisture contents were heated at 80° C., 100° C., 130° C. and 160° C. under atmospheric pressure by means of the apparatus described above and then after reaching each temperature, each of these heated powders was maintained for 2 hours at each heating temperature while stirring. Then, the water solubility of each powder, as prepared above, at each of the above temperatures was measured by taking 2 g of each powder and dissolving it in 50 cc of water and removing the insoluble matter by filtration. The insoluble matter was dried at 105° C. until a constant weight was obtained and the dried product was weighed to calculate the percentage of water-soluble ingredients.

FIG. 1 shows the water solubilities of plasma powders with varying moisture contents. Line A represents the case of heating the plasma powders at 80° C.; line B represents the case of heating the plasma powders at 100° C.; line C represents the case of heating the plasma powders at 130° C. and line D represents the case of heating the plasma powders at 160° C. The results show that the heating temperatures used in sterilizing must be adjusted within the above range depending on the moisture content. When plasma powders having a moisture content of 30% or less are heated for 2 hours at a temperature of 130° C. or less, the heated powders have a water solubility of at least 50%, can be used as a binding agent for foodstuffs and provide good rheological properties. Likewise, when plasma powders having a moisture content of 10% or less are heated at 160° C., the heated powders have a water solubility of at least 50%. On the other hand, when plasma powders having a moisture content greater than 20% are heated at 160° C., the heated powders does not have a water solubility of 50% or more. Therefore, in the case of heating the plasma powders having a moisture content of 20% or more at 160° C., the object of the present invention cannot be achieved.

Figure 2:
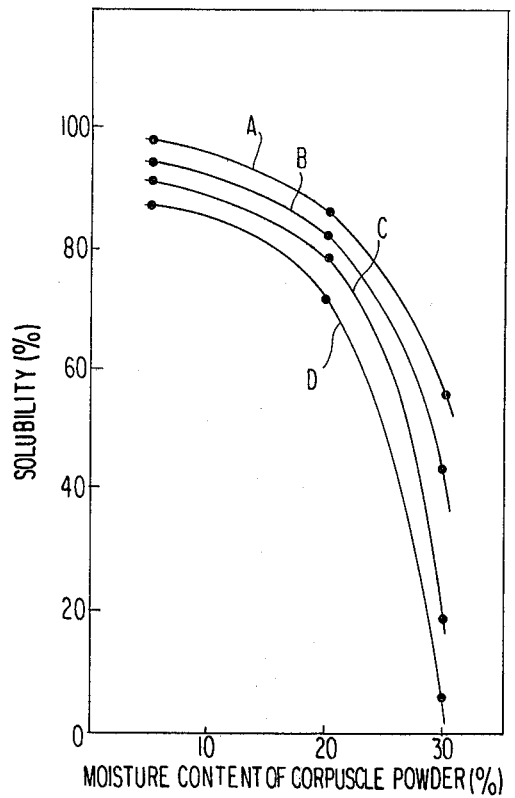
FIG. 2 is a graphical presentation showing the relationship, at different heating temperatures, between the moisture content of a corpuscle powder and the solubility of the corpuscle powder in water.

FIG. 2 shows the solubilities of corpuscle powders with varying moisture contents. Curves A, B, C and D illustrate the same relationships as to heating temperature used as in FIG. 1. The results show that corpuscle powders having a moisture content of 20% or less and heated for 2 hours at heating temperature of 80° to 160° C. have a solubility of 50% or more and are generally acceptable for a rheological binding agent of the foodstuffs. Likewise, the corpuscle powders having a moisture content of 30% are suitable when heated at heating temperature less than 100° C., but when the corpuscle powders having a moisture content of greater than 30% are heated at 100° C. or more, the solubility of these powders is less than 50% and, as a result, the object of the present invention can not be achieved. The solubility of the corpuscle is greatly influenced by the moisture content rather than the heating temperature as compared with the solubility of the plasma. In other words, when the moisture content of these powders is 20% or less, the reduction in solubility due to heating is small and, therefore, a moisture content of 20% or less is preferred in the case of corpuscle powders.

Figure 3:
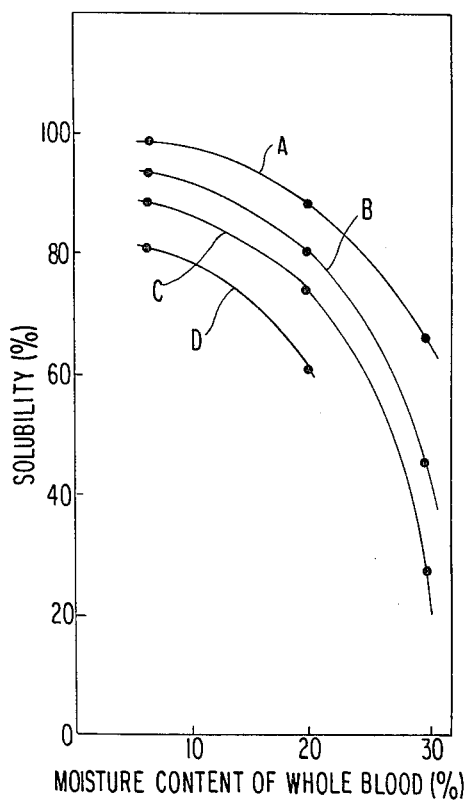
FIG. 3 is a graphical presentation showing the relationship, at different heating temperatures, between the moisture content of a whole blood powder and the solubility of the whole blood powder in water.

FIG. 3 shows the solubilities of whole blood powders with varying moisture contents. Curves A, B, C and D have the same meaning as in FIG. 1 as to heating temperature used. The results show that whole blood powders having a moisture content of 20% or less when heated for 2 hours at heating temperature of 80° to 160° C. have a solubility of 50% or more generally acceptable for a rheological binding agent of the foodstuffs. Likewise, whole blood powders having a moisture content of 30% are suitable when heated at heating temperature less than 100° C., but when the moisture content of the whole bood powders is greater than 30%, the solubility due to heating at 100° C. or more is less than 50% as same as in corpuscle and, as a result, the object of the present invention cannot be achieved.

Figure 4:
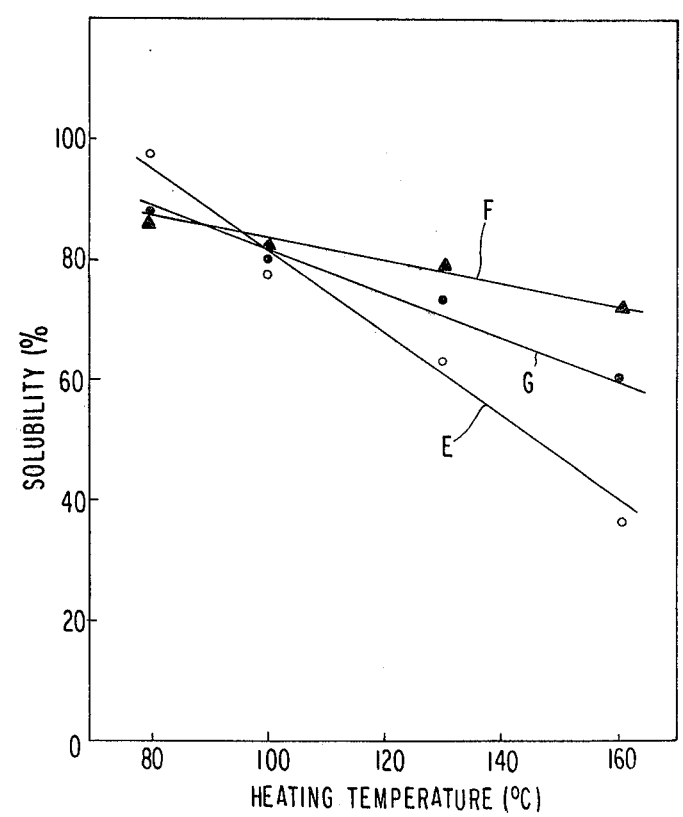
FIG. 4 is a graphical presentation showing the relationship between the heating temperatures for a plasma powder, corpuscle powder and a whole blood powder, each having a moisture content of 20% by weight and their solubility in water.

FIG. 4 shows the solubilities of plasma powders (E), corpuscle powders (F) and whole blood powders (G) having a moisture content of 20% which were heated for 2 hours at different temperatures. FIG. 4 shows the relationship between the water solubility and heating temperature at certain moisture contents (i.e., 20%). FIG. 4 shows that the plasma is more easily affected by heating in comparison with the corpuscle and the whole blood and even if the corpuscle and whole blood are heated for 2 hours at the specified temperature, the properties of the proteins are not affected since the solubility of the proteins is at least 50%. Further, FIG. 4 shows that if the plasma having a moisture content of 20% is heated for 2 hours at the heating temperature of about 145° C. or less, the properties of the proteins are not affected since the solubility of the proteins is at least 50%.

COMPARATIVE EXAMPLE 1

The relationship between the solubility and heating conditions of the blood powder having a moisture content of 30% or more was measured using a whole blood powder.

Three samples were prepared as follows:

Preparation of Three Samples

Cow flesh blood was collected without adding an anti-coagulant. Since the anti-coagulant was not added in the collected blood, about half of the collected blood was coagulated. The semi-coagulated blood was homogenized. The blood used was not divided into blood plasma and blood corpuscle. 1 l of a whole blood was introduced into the 2 l volume flask for concentration to concentrate the collected and homogenized whole blood. That is, the homogenized whole blood was concentrated under vacuum conditions by means of a rotary-evaporator. The whole blood was heated in the water bath maintained at 55° C. until the whole blood reached the intermediate tacky state (as defined below) and further concentrated by increasing the temperature of the water bath to about 80° C. until the tacky state was complete.

The concentration was carried out by adjusting the vacuum within the range of 32 mm Hg to 45 mm Hg using a vacuum manometer. When the temperature of the water bath was 55° C., the pressure was 32 mm Hg and when the temperature of the water bath was 70° C., the pressure was 45 mm Hg. In accordance with the above method, the following samples were obtained.

(a) Initial tacky state (Sample 1)

As the blood is concentrated, the viscosity of the blood increases. When the whole blood adheres to the inner wall as the concentration flask is rotated and the adhered blood flows down along the inner wall, this was considered the initial point of a tacky state.

Before the initial point, the blood does not adhere to the inner wall.

(b) The intermediate tacky state (Sample 2)

The intermediate tacky state is defined as the condition where the blood flows slowly along the inner wall of a rotated flask.

(c) The final tacky state (Sample 3)

The final tacky state is defined as the state when the fluidity of the concentrate is completely lost, the concentrate solidifies and the blood cannot flow along the inner wall.

The samples are referred to as Samples 1 to 3 below and correspond to the INITIAL, INTERMEDIATE and FINAL tacky states, respectively, as defined above.

A blood powder Sample 4 having a moisture content of 30% in accordance with the present invention was prepared by crushing the FINAL tacky state concentrate, with a mortar, introducing the crushed blood concentrate into a concentrating flask and drying to a moisture content of 30% with a water bath maintained at 80° C. under vacuum.

Measurement of concentrate temperature

Temperature (i.e., material temperature) of the concentrates in each of the above items (a), (b) and (c), and the blood powder having a moisture content of 30% was measured by removing the flask from a rotary evaporator, maintaining the flask in a water bath at a specified bath temperature, and inserting a thermometer into the blood.

The temperature of the blood and the bath measured during preparation of the concentrates are shown in Table 1 below.

TABLE 1

| | Initial Tacky State | Intermediate Tacky State | Final Tacky State | Concentrate Having a Moisture Concentration of 30% |
|---|---|---|---|---|
| Internal Blood Temperature | 38 | 43 | 48 | 55 |
| Ambient Temperature (i.e., temp. of water bath) | 55 | 55 | 80 | 80 |

Each of Samples 1 to 3 was heated to 60° C., 70° C. and 80° C. under atmospheric pressure while stirring and the heating at each temperature was continued for 10 minutes to provide heated concentrates. Sample 4, a blood powder having a moisture content of 30%, was heated to 80° C. under atmospheric pressure while stirring and the heating at temperature of 80° C. was continued for 10 minutes.

The solubility of each sample, as prepared, at each of the above temperatures was then measured by taking 2 g of each sample and dissolving it in 50 cc of water and removing the insoluble matter by filtration. The insoluble matter was dried at 105° C. until a constant weight was obtained and the dried product was weighed to calculate the percentage of water-soluble ingredients. These percentages are set forth in Table 2.

TABLE 2

| | Samples 1 to 4 as Prepared | | Heated Samples 1 to 4 % Water Soluble | | |
|---|---|---|---|---|---|
| | Moisture content | % Water Soluble | 60° C.* | 70° C.* | 80° C.* |
| Initial Tacky State (Sample 1) | 63.5 | 85.5 | 60.7 | 12.6 | 2.6 |
| Intermediate Tacky State (Sample 2) | 47.7 | 83.4 | 73.4 | 19.7 | 5.0 |
| Final Tacky State (Sample 3) | 38.3 | 79.7 | 75.4 | 35.4 | 18.6 |
| Present Invention (Sample 4) | 29.7 | 78.3 | — | — | 56.3 |

*The temperature of blood itself.

As is apparent from Table 2, when the blood powder having a moisture content of 30% (Sample 4) is heated at 80° C., the water solubility of 56.3% can be retained, whereas when the blood powder having a moisture content of 38.3% (Sample 3) in the final tacky state, is heated at 80° C., the water solubility is remarkably reduced to 18.6%. That is, even if the difference of a moisture content is as small as 8.6%, 67.0% (i.e., $$\left(100 - \frac{18.6}{56.3} \times 100\right) \%$$

of water solubility is remarkably lost. The blood powder having a moisture content of 38.3% is not useful for foodstuff. Therefore, in the relationship between the moisture content and the solubility, it is apparent from Table 2 and FIGS. 1, 2 and 3 that the moisture content of 30% is very critical.

Accordingly, in the relationship of the heating temperature, the moisture content, the solubility and the sterilization, the at least 50% solubility acceptable for foodstuff was obtained in the condition of the heating temperatures of 80° C. to 160° C. and the moisture contents up to 30%, i.e., the combinations of the heating temperature, the moisture content and a kind of the powder (i.e., plasma, corpuscle and whole blood). Further, a minimum 50% solubility was obtained whenever the heating temperatures of 100° to 130° C. and the moisture contents of 20% or less were combined.

EXAMPLE 2

A plasma powder having a moisture content of 9.7% was prepared by spray drying plasma. A small amount of powder was sampled from the resulting plasma powder, and the number of bacteria present in the sample and the water solubility and heat coagulability of the resulting plasma powder were measured. The remainder was put into a batch-type stirred heating device.

The temperature of the plasma powder was increased to 105° C. with the temperature being monitored. Then, the plasma powder was maintained at a temperature of 105° C., and sampled every 5 minutes over a 10 minute period. The number of bacteria in each of these samples, and the water solubilities and heat coagulabilities of each of these samples were measured. The results obtained are shown in Table 3 below.

The number of bacteria, the solubility and the heat coagulability were measured using the following methods.

The number of bacteria was determined both for viable bacteria and Coliform bacteria. The number of viable bacteria was that of the number of bacterial cells found in 1 g of sample, and the number of Coliform bacteria was measured using the most probable number (M.P.N.) method.

The solubility was measured in the following manner. 2 g of a sample blood powder was dissolved in 50 cc of water, and after removing the insoluble matter by filtration, the insoluble matter was dried at 105° C. until a constant weight was obtained. The dried product was weighed to calculate the percentage of the water-soluble ingredients.

The heat coagulability was measured in the following manner.

2 g of a blood powder sample was dissolved in 50 cc of water. After removing the insoluble matter by filtration, the clear solution was heated to 100° C. and maintained at this temperature for 1 minute. After the heating, heat-coagulated ingredients were centrifugally settled, and the volume of these ingredients was measured. the volume measured is expressed as an index against the volume of the blood powder before heating which was taken as 100.

TABLE 3

| Sample Maintenance Time at Specified Temperature | Number of Coliform Bacteria | Number of Viable Bacteria | Solubility (%) | Heat Coagulability (%) |
|---|---|---|---|---|
| Before Heating | 2.4 × 10$^2$ | 2.4 × 10$^3$ | 89.5 | 100 |
| 0 Minute* | <3 | <300 | 82.9 | 97 |
| 5 Minutes | <3 | <300 | 82.6 | 95 |
| 10 Minutes | <3 | <300 | 80.8 | 95 |

*"0 Minute" shows the results at the time which the specified temperature was reached.

EXAMPLE 3

A corpuscle powder having a moisture content of 11.1% was prepared by lyophilization. The corpuscle powder was treated in the same manner as described in Example 2, and the number of bacteria, the water solubility and the heat coagulability before heat treatment and after heat treatment at heating temperature of 110° C. were measured. The results obtained are shown in Table 4 below.

TABLE 4

| Sample Maintenance Time at Specified Temperature | Number of Coliform Bacteria | Number of Viable Bacteria | Solubility (%) | Heat Coagulability (%) |
|---|---|---|---|---|
| Before Heating | 7.5 × 10$^2$ | 3.5 × 10$^3$ | 89.6 | 100 |
| 0 Minute | <3 | <300 | 83.0 | 96 |
| 5 Minutes | <3 | <300 | 82.7 | 96 |
| 10 Minutes | <3 | <300 | 92.4 | 96 |

EXAMPLE 4

A whole blood powder having a moisture content of 4.7% was prepared by vacuum drying. The whole blood powder was treated in the same manner as described in Example 2, and the number of bacteria, the water solubility and the heat coagulability before heat treatment and after heat treatment at heating temperature of 115° C. were measured. The results obtained are shown in Table 5 below.

TABLE 5

| Sample Maintenance Time at Specified Temperature | Number of Coliform Bacteria | Number of Viable Bacteria | Solubility (%) | Heat Coagulability (%) |
|---|---|---|---|---|
| Before Heating | 3.5 × 10$^2$ | 5.5 × 10$^3$ | 90.8 | 100 |
| 0 Minute | <3 | <300 | 79.1 | 87 |
| 5 Minutes | <3 | <300 | 77.7 | 86 |
| 10 Minutes | <3 | <300 | 77.0 | 86 |

EXAMPLE 5

A corpuscle powder having a moisture content of 5.7% was prepared by spray drying. This corpuscle powder was treated in the same manner as in Example 2, and the number of bacteria, the water solubility and the heat coagulability before heat treatment and after heat treatment at heating temperature of 125° C. were measured. The results obtained are shown in Table 6 below.

TABLE 6

| Sample Maintenance Time at Specified Temperature | Number of Coliform Bacteria | Number of Viable Bacteria | Solubility (%) | Heat Coagulability (%) |
|---|---|---|---|---|
| Before Heating | $2.0 \times 10^2$ | $3.8 \times 10^3$ | 86.7 | 100 |
| 0 Minute | <3 | <300 | 79.6 | 92 |
| 5 Minutes | <3 | <300 | 79.1 | 92 |
| 10 Minutes | <3 | <300 | 78.5 | 90 |

EXAMPLE 6

A serum powder having a moisture content of 0.2% was prepared by vacuum drying. The serum powder was treated in the same manner as described in Example 2, and the number of bacteria, the water solubility and the heat coagulability before heat treatment and after treatment at heating temperature of 110° C. were measured. The results obtained are shown in Table 7 below.

TABLE 7

| Sample Maintenance Time at Specified Temperature | Number of Coliform Bacteria | Number of Viable Bacteria | Solubility (%) | Heat Coagulability (%) |
|---|---|---|---|---|
| Before Heating | $4.4 \times 10^2$ | $9.3 \times 10^3$ | 91.0 | 100 |
| 0 Minute | <3 | <300 | 81.1 | 93 |
| 5 Minutes | <3 | <300 | 80.8 | 93 |
| 10 Minutes | <3 | <300 | 79.9 | 93 |

The results given in Tables 1 to 6 show that blood powders can be sufficiently sterilized within very short periods of time at heating temperature of as high as 100° C. or more, and the sterilized powders are soluble and heat coagulable, so are useful for human consumption.

EXAMPLE 7

A serum powder having a moisture content of 6.9% was prepared by lyophilization. A small amount of the powder was sampled from the serum powder obtained, and the number of bacteria present in the sample and the solubility in water and heat coagulability of the serum powder were measured.

The remainder was placed in a continuous-type stirred heating device. This heating device was so designed that in about 10 minutes after the introduction of the serum powder, the temperature of the serum powder reached 110° C., and then, while the serum powder was maintained at 115° C., the serum powder was conveyed to reach the exit of the device 5 minutes later and was discharged through the exit. At the exit of this continuous-type stirred heating device, the heated powder was sampled six times every 10 minutes beginning 1 hour after the start of the operation. The number of bacteria, the water solubility and the heat coagulability were measured in the same manner as in Example 2. The results obtained are shown in Table 8 below.

TABLE 8

| Sample No. | Number of Coliform Bacteria | Number of Viable Bacteria | Solubility (%) | Heat Coagulability (%) |
|---|---|---|---|---|
| Before Heating | $9.3 \times 10^2$ | $3.9 \times 10^3$ | 91.2 | 100 |
| 1 | <3 | <300 | 79.5 | 89 |
| 2 | <3 | <300 | 78.5 | 87 |
| 3 | <3 | <300 | 78.6 | 87 |
| 4 | <3 | <300 | 79.0 | 88 |
| 5 | <3 | <300 | 78.9 | 88 |
| 6 | <3 | <300 | 79.6 | 89 |

EXAMPLE 8

A blood corpuscle powder having a moisture content of 4.5% was prepared by vacuum drying. The corpuscle powder was treated in the same manner as in Example 5, and the number of bacteria, the water solubility and the heat coagulability before heat treatment and after heat treatment at heating temperature of 120° C. for 5 minutes with a period of 10 minutes over which the temperature was increased were measured. The results obtained are shown in Table 9 below.

TABLE 9

| Sample No. | Number of Coliform Bacteria | Number of Viable Bacteria | Solubility (%) | Heat Coagulability (%) |
|---|---|---|---|---|
| Before Heating | $5.3 \times 10^2$ | $6.8 \times 10^3$ | 87.3 | 100 |
| 1 | <3 | <300 | 81.3 | 94 |
| 2 | <3 | <300 | 80.3 | 94 |
| 3 | <3 | <300 | 80.1 | 94 |
| 4 | <3 | <300 | 79.9 | 92 |
| 5 | <3 | <300 | 80.8 | 94 |
| 6 | <3 | <300 | 80.9 | 94 |

The results in Tables 8 and 9 show that in a continuous process, blood powders can be sterilized in a stable manner with a good sterilizing effect while minimizing the reduction in solubility and the heat coagulability if the heating temperature and time are maintained constant.

While the invention has been described in detail and with reference to specific embodiments thereof, it will be apparent to one skilled in the art that various changes and modifications can be made therein without departing from the spirit and scope thereof.

What is claimed is:

1. A method for reducing the bacterial population of a blood powder without substantially heat denaturing the blood protein in said powder or degrading the water solubility or heat coagulability of said blood protein during said method for reducing the bacterial population, which comprises heating said blood powder which has a moisture content of about 30% by weight or less at a temperature of about 80° to 160° C. for a period of time to reduce the bacterial population of said blood powder so as to obtain blood products having a solubility of at least 50%.

2. The method of claim 1, wherein the powder is a plasma powder, a serum powder, a corpuscle powder, or a whole blood powder.

3. The method of claims 1 or 2, wherein the heating temperature is 90° to 145° C.

4. The method of claims 1 or 2, wherein the heating temperature is 100° to 130° C.

5. The method of claims 1 or 2, wherein the heating temperature is 80° to 100° C.

6. The method of claims 1 or 2, wherein the heating temperature is 80° to 130° C.

7. The method of claims 1 or 2, wherein the heating temperature is 80° to 145° C.

8. The method of claims 1 or 2, wherein the blood powder has a moisture content of 20% by weight or less.

9. The method of claims 1 or 2, wherein the blood powder has a moisture content of 10% by weight or less.

10. The method of claims 1 or 2, wherein the blood powder has a moisture content of 20% by weight or less and the heating temperature is 80° to 130° C.

11. The method of claims 1 or 2, wherein the blood powder has a moisture content of 20% by weight or less and the heating temperature is 80° to 145° C.

12. The method of claims 1 or 2, wherein the heating is performed for about 4 hours or less.

13. The method of claims 1 or 2, wherein the heating is performed for about 10 minutes or less.

14. The method of claims 1 or 2, wherein the heating is performed for about 5 to 10 minutes.

15. The method of claim 1, wherein the heating temperature is a temperature of the blood powder itself.

16. The method of claim 1, wherein the number of viable bacteria is reduced to less than 300/g of the product of the method.

* * * * *